United States Patent
Stephenson

(10) Patent No.: US 7,676,386 B2
(45) Date of Patent: Mar. 9, 2010

(54) SYSTEMS AND METHODS FOR SCHEDULING AND SEQUENCING SESSIONS OR APPOINTMENTS

(75) Inventor: Hugo Stephenson, Princeton, NJ (US)

(73) Assignee: Quintiles Transnational Corp., Durham, NC (US)

( * ) Notice: Subject to any disclaimer, the term of this patent is extended or adjusted under 35 U.S.C. 154(b) by 0 days.

(21) Appl. No.: 11/644,302

(22) Filed: Dec. 22, 2006

(65) Prior Publication Data
US 2007/0250344 A1 Oct. 25, 2007

Related U.S. Application Data

(60) Provisional application No. 60/753,867, filed on Dec. 22, 2005.

(51) Int. Cl.
G06Q 10/00 (2006.01)
G06Q 50/00 (2006.01)
G06Q 40/00 (2006.01)
A61B 5/00 (2006.01)
G06F 19/00 (2006.01)

(52) U.S. Cl. .................. 705/3; 705/2; 705/4
(58) Field of Classification Search ......... 705/2, 705/3, 4
See application file for complete search history.

(56) References Cited

U.S. PATENT DOCUMENTS

| | | | | |
|---|---|---|---|---|
| 5,319,543 A * | 6/1994 | Wilhelm | ......................... | 705/3 |
| 5,572,421 A * | 11/1996 | Altman et al. | ................... | 705/3 |
| 5,597,995 A * | 1/1997 | Williams et al. | ............. | 235/375 |
| 5,666,490 A * | 9/1997 | Gillings et al. | .............. | 709/238 |
| 5,748,907 A * | 5/1998 | Crane | ............................. | 705/2 |
| 5,809,477 A | 9/1998 | Pollack | | |
| 5,991,731 A * | 11/1999 | Colon et al. | ................... | 705/3 |
| 6,047,259 A * | 4/2000 | Campbell et al. | .............. | 705/3 |
| 6,311,162 B1 * | 10/2001 | Reichwein et al. | ............. | 705/1 |
| 6,334,192 B1 * | 12/2001 | Karpf | ............................. | 714/1 |
| 6,338,039 B1 * | 1/2002 | Lonski et al. | ................... | 705/3 |
| 6,356,873 B1 * | 3/2002 | Teagarden et al. | ............. | 705/3 |
| 6,381,576 B1 * | 4/2002 | Gilbert | ........................... | 705/2 |
| 6,850,889 B1 * | 2/2005 | Zayas, Jr. | ........................ | 705/3 |
| 7,054,823 B1 | 5/2006 | Briegs et al. | | |
| 2003/0065669 A1 * | 4/2003 | Kahn et al. | ................. | 707/100 |
| 2004/0010418 A1 | 1/2004 | Buonocore et al. | | |
| 2004/0093240 A1 | 5/2004 | Shah | | |
| 2006/0036478 A1 | 2/2006 | Aleynikov et al. | | |
| 2006/0143047 A1 | 6/2006 | Briegs et al. | | |

FOREIGN PATENT DOCUMENTS

WO WO0193178 12/2001
WO WO 2004/038560 5/2004

* cited by examiner

*Primary Examiner*—Gerald J O'Connor
*Assistant Examiner*—Amber L Altschul
(74) *Attorney, Agent, or Firm*—Kilpatrick Stockton LLP

(57) ABSTRACT

Embodiments of the present invention provide systems and methods for scheduling patients in an organized and uniform way using a batch follow-up system. Such batch follow-up methods help a research site conducting research to prepare one or more of study supplies, patient charts, study goals, and data collecting requirements in preparation for the batch follow-up visits. Embodiments of the invention also relate to systems and methods for communicating initial and follow-up visit dates to patients. In certain instances, various communications (e.g., between the patients and the study site or between the study site and the study sponsor) may be electronic communications. Methods of scheduling and sequencing patient visits may be conducted over a network wherein reminders about follow-up visits are electronically generated.

20 Claims, 2 Drawing Sheets

SYSTEMS AND METHODS FOR SCHEDULING AND SEQUENCING SESSIONS OR APPOINTMENTS

This application claims the benefit of U.S. Provisional Application Ser. No. 60/753,867, filed Dec. 22, 2005 titled "Systems and Methods for Scheduling Sessions or Appointments," the entire contents of which are hereby incorporated by reference.

FIELD OF THE INVENTION

The present invention relates generally to systems and methods for scheduling and sequencing follow-up sessions or appointments, particularly follow-up sessions for patients involved in research, clinical trials, or treatment programs.

BACKGROUND

In clinical research, such as pharmaceutical research, medical device research, psychology research, or any other human-based study or research, patients are often required to be present for multiple office visits. Some of these visits to an office or research location may entail being administered a drug or a placebo. Other visits may be a follow-up session or appointment where the patient's vital signs (e.g., blood pressure, weight, temperature, etc.) or other indicia (e.g., white blood cell count, eye dilation, etc.) may be taken and recorded.

Often, during such studies, the return visits are scheduled for a certain number of days, weeks, or months from the initial treatment day. For example, if an experimental drug was administered on day "0," the patient may be required to return for follow-up visits at days 7, 14, 21 or on months 3, 6, and 9, and so forth. Scheduling and staffing these follow-up visits can cause many challenges.

For example, research sites often run more than one study at a time. To schedule multiple return visits for multiple studies can be a daunting task. First, different parameters need to be measured for different studies and protocols. One study may require blood testing, which means one set of supplies and staff with a certain expertise are needed, while another study may require an x-ray and an oral exam, requiring another set of supplies and staff with a different expertise. If these return visits are scheduled relative to the first visit (which fall on different days for different patients), return visits will also fall on different days, and research sites must be prepared and trained to conduct these return visits on many different occasions. This can be expensive and difficult to manage, and often deters smaller facilities from taking on multiple studies. Second, follow-up visits may require the presence of specialized staff or equipment, which means that these resources need to be dispatched to various sites on a very frequent basis. If these return visits are scheduled relative to a patient's first visit (which fall on different days for different patients), personnel and supplies are constantly being shuttled from location to location. This adds to the cost of conducting studies, because the resources needed to manage a research site are not controlled. It also means that the needs of a research site cannot be easily anticipated. The administrative challenges that are already inherent in conducting research are multiplied. However, it is often to a research company's advantage to keep the research site burden as low as possible. When this burden is lowered, data collection is easier, which can help improve the quality of data. For example, there will likely be fewer follow up queries, which many happen when a researcher sees one patient for one study and collects one type of data, and immediately afterward, sees another patient from a separate study and needs to collect a completely different set of data. In this example, the researcher may forget to take the blood pressure of the second patient in the second study because blood pressure was not required to be taken from the first patient in the first study. This "break" in flow can cause mistakes and difficulties. Third, longer studies often experience a high patient drop-out rate. Patients may begin to tire of the appointments or feel like they are participating in the study all alone, and decide to drop out. This causes multiple problems in the collecting of data, because long-term data may be unavailable. Additionally, the FDA and other organizations may imply that an adverse event occurred if follow-up data is not available for a particular patient, even though the patient may be doing well or has even improved, but simply failed to return for collection of follow-up data.

Consider the following example. If a patient in a study is required to return for a follow-up visit every three months for a year, currently, he or she would be told to call the research site or facility at about the 2½ month mark to schedule the next appointment. The patient may forget to call, which requires staff to actively conduct follow-up contact. In any event, there needs to be a receptionist or scheduler on-hand to make each appointment. If a site is working with a large number of patients on a study (e.g., with 10, 50, or 100 patients), the research site may need to coordinate 40, 200, or even 400 individual follow-up visits distributed randomly over the course of a year. Moreover, the patients are likely to all schedule on different days, which means that specific supplies need to be set out multiple times, detailed protocols may need to be re-reviewed before each follow-up day, and specialty staff may spend unnecessary time traveling to different sites throughout the week or month. In this example, if there are 10 patients in this study, and each requires 4 follow-up visits, and there is one scheduling contact and one appointment contact for each visit, there would be over 80 patient contacts. This is time-consuming and may likely lead to higher costs and inefficiencies.

Accordingly, there is a need for a system and method for scheduling patients in an organized and uniform way, preferably using a batch follow-up system. There is a further need for a system and method to improve patient retention. There is a further need to reduce scheduling costs and patient scheduling contacts.

SUMMARY OF THE INVENTION

Embodiments of the present invention relate to systems and methods for scheduling patients in an organized and uniform way using a batch follow-up system. For example, the study site and/or study sponsor may work together to determine the number and nature of follow-up visits that will be required after each patient's initial visit for a particular study. Then they may identify a start date for the initial visit, identify follow-up visit dates to be conducted after the initial visit in batches; and conduct batch follow-up visits in the identified batches. The batch follow-up methods help a research site conducting research to prepare one or more of study supplies, patient charts, study goals, and data collecting requirements in preparation for the batch follow-up visits.

Embodiments also relate to systems and methods for communicating initial and follow-up visit dates to patients. In certain instances, various communications (e.g., between the patients and the study site or between the study site and the study sponsor) may be electronic communications. For example, methods of scheduling and sequencing patient visits may be conducted over a network wherein reminders about follow-up visits are electronically generated.

DETAILED DESCRIPTION

Embodiments of the present invention provide methods and systems for scheduling patients in a uniform and organized way, helping to improve patient retention and lower study costs and inefficiencies. Specific embodiments relate generally to systems and methods for batch follow-up sequencing and scheduling. These systems allow research sites to concentrate their efforts into a few, discrete activities per day, week or month that are intended to improve study performance and lower study costs and investigator fees. They are also intended to reduce site workload through more efficient follow-up. Such systems are further intended to reduce staff workload by concentrating site communications and required on-site staff during active periods at the site. They are further intended to simplify communication patterns with sites and patients, and potentially with a research sponsor.

Figure 1:
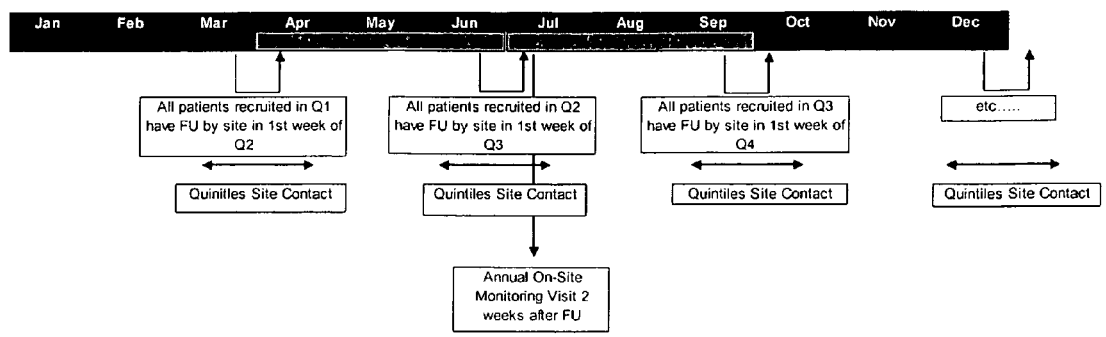
FIG. 1 shows a flow chart representing one embodiment for batch follow-up appointment sequencing.
Figure 2A:
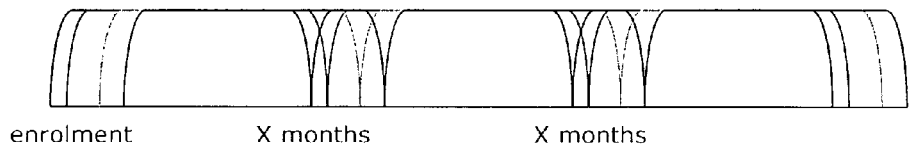
FIG. 2A shows an example of the prior art random scheduling methods.
Figure 2B:
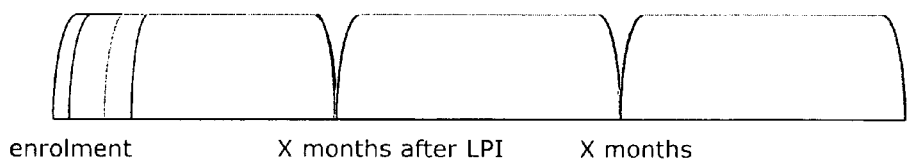
FIG. 2B shows an example of one embodiment for batch follow-up methods.

In one embodiment, the systems and methods relate to scheduling patients to return for site visit follow-ups at pre-established dates. For example, if all patients are enrolled in a study over a few weeks or months, they are scheduled to return for follow-up on a particular date. If quarterly visits are required, then follow-ups may be scheduled in batches on Mar. 1, Jul. 1, Sep. 1, and Dec. 1, as shown in FIG. 1. Of course, if more patients are involved in the study than can be seen in one day, the follow-up visits may be scheduled during a certain week and/or month. These batches may be one particular day or throughout a particular week (or series of weeks), depending upon the nature of the study and the nature of the follow-up required. These pre-determined dates may be determined based on the needs of the study and may be communicated to the patients preferably at the time they enroll in the study or preferably soon afterward. This communication may be verbal, via a letter, or via any electronic means, described in more detail below. The benefits of such follow-up sequencing include a patient being able to pre-mark certain dates that will be site visit dates. Knowing these specific dates in advance can help improve patient retention. Additionally, as groups of patients are seen on similar days, they may develop a camaraderie that can help patient retention as well. Additional benefits of batch follow-up sequencing are that the site can be prepared to see all patients for one study in a condensed time span (e.g., on one day, week, or month) and all study supplies, study personnel, patient charts, study goals, and data collecting requirements can be set out and ready. The data collection can be more efficient because the same information will be collected from the patients being seen on those days. The site can better plan its workload, and it can make any necessary site monitoring (on-site or remote) more efficient and organized. FIG. 2A shows an example of how studies have been completed in the past, with patients having the initial visit on the enrollment date, and subsequent visits being calculated from the enrollment date. As shown, this causes subsequent visits to be scheduled sporadically, e.g., throughout a week, month, or year. FIG. 2B shows the improvement method described herein, in which all patients are enrolled over a certain time, but the initial visit is scheduled in a condensed time (e.g., on the same day or during the same week), allowing subsequent visits to also be scheduled in a condensed time.

In a specific embodiment, one way to organize this batch follow-up sequencing is to
(a) determine the number and nature of follow-up visits required after an initial visit;
(b) identify a start date for the initial visit;
(c) identify follow-up visit dates to be conducted after the initial visit in batches; and
(d) conduct batch follow-up visits in the identified batches.

For example, patients can be recruited for the study on a rolling basis—the "initial visit" date may already be identified and communicated or the patients may sign up and wait for notification of the initial visit date. If the initial visit date has not been previously identified, before the initial visit (in many cases, two weeks or more before the initial visit), the site will contact and schedule patients for the initial visit. The organization sponsoring the study may call the site and remind them to record certain data during this (and subsequent) visits.

In certain embodiments, the pre-determined dates may be selected via an algorithm or formula, which may be implemented manually and/or with the assistance of computer automation, that considers when all patients were enrolled (assuming that the enrollment date for each patient is that date that the experimental treatment was administered) and calculates an appropriate follow-up date that is either in the middle of the enrollment dates or that is a certain time out from the enrollment dates, again, depending upon the need of the particular study. In other embodiments, the follow-up dates may be pre-set before the study begins or as the study progresses. In further embodiments, it may be useful to schedule visits within an interval or a few days (e.g., over a particular week) if that patient population is large.

In another embodiment, all enrolled patients receive the prescribed study treatment on the same day, allowing the batch follow-up days to be calculated an exact number of days from the delivery of treatment. (This embodiment may be less desirable in cases where it is more convenient or otherwise more beneficial to deliver the treatment on the enrollment date, however it may be useful in certain instances.)

Of course, if there are adverse events before a batch follow-up date or appointment arrives, it is envisioned that a patient may need to return for a site visit at an unscheduled time. It may be possible to set aside "emergency" or "adverse event" days so that the staff of the study can be prepared for walk-ins (e.g., study supplies set up, etc.).

It is particularly preferred to use the systems and methods described herein for longer-term studies for which follow-up is not required to take place at a particular day-mark (e.g., check-in at 3-4 months vs. check-in at 7 days after treatment to see how quickly the effects take place or the speed of action), unless all patients are enrolled on the same day. It should be understood, however, that this invention is not intended to be limited to longer-term studies.

The systems and methods of embodiments of this invention allow a research site to set aside a half-day, a full day, a few days, or an entire week to focus on collecting data for a particular study. If blood needs to be drawn and tested, the supplies can be ready, the appropriately-trained personnel can be on-site, and the lab can be ready with the proper protocol and indices to be tested and reviewed. Seeing the patients during a contained or condensed time period or in a batch follow-up sequence system lessens study costs and administrative fees. These systems and methods can also increase the incentive for research sites to take on smaller studies or for companies to run smaller studies that might otherwise be cost prohibitive due to difficult follow-up.

The systems and methods described also alleviate the need for a separate scheduling procedure for each patient for each visit. In some cases, scheduling can be automated through computer systems and methods that process, schedule, and notify patients of appointments. Both automated and manual systems and methods provide advance notice and allow the patient to clear his or her calendar for follow-up visits well in advance. In short, batch follow-up may help improve patient retention by (a) giving them notice of when the next appointment will be and (b) creating a sense of camaraderie within the group—study patients see each other at the same follow-up visits, which gives them more of a "we're all in this together" feeling, preferably preventing patients from tiring of the study and ultimately dropping out. The built-in critical mass adds an advantage over ad-hoc appointments.

It is possible to manage this system manually or over a network or computer system to set and distribute the scheduling information. It is also possible for any algorithm that may be used to set a series of one or more preferred scheduling dates to be done via a computer system.

Continuing with the above example, once the study is set to begin, the study sponsor may send the site a link to an electronic database in which to record data. (This database may also be used for scheduling, as discussed below.) The investigator may pull charts of an enrolled patients, transcribe data from each patient chart into the electronic database system. Once the initial visit and subsequent visits have been conducted, the database can send a thank you to the site or a reminder to complete forms. This process is completed after the initial visit and then may be completed after each subsequent batch follow-up visit.

Figure 3:
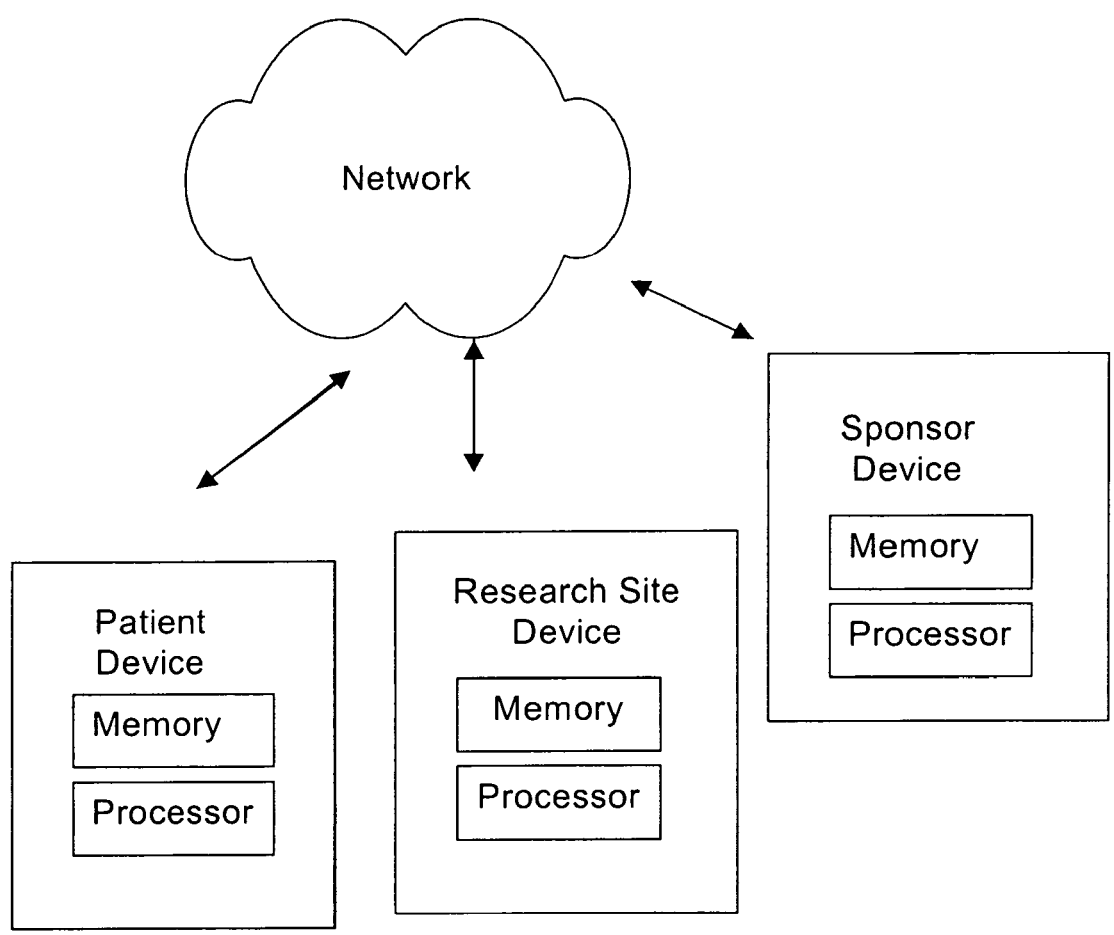
FIG. 3 shows an example of how the batch follow-up scheduling can be completed by an automated system, such as computers that communicate over a network.

Referring to another embodiment, the scheduling process may take place electronically. For example, the block diagram at FIG. 3 shows messages and other scheduling information and data flowing between various computers on a network. The network includes one or more devices, one of which may be a research site device or server run by the coordinating research organization or research facility and one of which may be a patient's computing device (e.g., home computer or PDA) and/or the sponsoring company's device, or any other system relevant and useful in connection with the embodiments described. Users may authenticate on a network by supplying the proper credentials (e.g., a general password, a password specific to the particular study, a personal ID number (PIN), and/or token).

Users may view, receive, and/or send scheduling information to and from other devices networked to the system electronically or any other means. A research facility computing device may execute software and other processes to identify a preferred or optimal scheduling date and/or distribute scheduling information to users via the network. In one embodiment, appointments may be sent and accepted using conventional software such as Microsoft Outlook or may be published on a website accessible to remote users. These appointments may be accepted and then automatically entered into the patients' calendars or PDAs.

Various systems in accordance with the present invention may be constructed. FIG. 3 shows an illustrative environment for implementation of one embodiment of the present invention. In this specific embodiment, the system comprises a patient device in communication with a research site device, which may optionally be in communication with a sponsor device. It should be noted that these labels are used for the sake of convenience only, and the research site device could be the sponsor device if the sponsor is running the study. Any of the computing devices described herein could be a PDA, personal computer, digital assistant, cellular phone, mobile phone, smart phone, pager, digital tablet, laptop computer, Internet appliance, or any other processor-based device. Examples of potential systems that may be used in connection with any embodiments are any processors coupled to a computer-readable medium, such as memory. Examples of operating systems are Microsoft® Windows®, Linux, or any other appropriate system. Potential devices may be a personal computer executing a browser application program such as Microsoft Corporation's Internet Explorer™, Netscape Communication Corporation's Netscape Navigator™, Mozilla Organization's Firefox, Apple Computer, Inc.'s Safari™, Opera Software's Opera Web Browser, the open source Linux Browser, and e-mail systems such as Microsoft Outlook.

The research site device may be an access point or a communication hub for remote devices connecting to network. The research site device or access point may be a dedicated hardware device or may be a general-purpose computer executing access point software. The research site access point may be wired or wireless and preferably includes a processor and memory. The processor part of the devices may be a microprocessor, or an ASIC, or may be in communication with computer-readable media, which stores program code or instructions that, when executed by the processor, cause the processor to perform actions. Embodiments of computer-readable media include, but are not limited to, an electronic, optical, magnetic, or other storage or transmission device capable of providing a processor with computer-readable instructions. Other examples of suitable media include, but are not limited to, a floppy disk, CD-ROM, DVD, magnetic disk, memory chip, ROM, RAM, an ASIC, a configured processor, optical media, magnetic tape media, or any other suitable medium from which a computer processor can read instructions. Also, various other forms of computer-readable media may transmit or carry program code or instructions to a computer, including a router, private or public network, or other transmission device or channel, both wired and wireless. The memory preferably includes software code for accessing the network. For example, the memory may include software code for supporting Dynamic Host Configuration Protocol (DHCP) and supporting Hypertext Transfer Protocol (HTTP) administrative access to the research site access point. Access points are available from a variety of manufactures, such as, for example, Linksys.

It should be noted that embodiment of the present invention may comprise systems having a different architecture than that shown in FIG. 3. In some embodiments, the automated process may replace the need to send paper reminders or make phone calls, and the research site device could generate a scheduling list and share it with patients and the sponsor via any electronic means. The information to be shared could be any compilation of dates, locations, items to bring, items to set up, personnel to be on site, tests to be run, future follow-up dates, newsletters and additional information to be communicated, requests for future studies, data from study or any other type of information. In general, systems and methods for scheduling batch follow-up sessions may be automated or facilitated by the use of a computer, device, or network system.

It should also be understood that although an automated scheduling process has been described herein, it is also possible for the scheduling procedure to take place manually, using appointment books and the like.

The foregoing description of the embodiments, including preferred embodiments, of the invention has been presented only for the purpose of illustration and description and is not intended to be exhaustive or to limit the invention to the precise forms disclosed. Changes and modifications, additions and deletions may be made to the structures and methods recited above and shown in the drawings without departing from the scope or spirit of the invention.

What is claimed is:

1. A method for scheduling batch follow-up visits for a plurality of patients participating in a clinical trial, comprising:
   (a) determining a number of follow-up visits after an initial visit for each patient of the plurality of patients participating in the clinical trial conducted at a research site;
   (b) identifying a first follow-up visit date for a first follow-up batch visit for each patient of the plurality of patients, the first follow-up visit date for each patient of the plurality of patients being within a first time window, wherein the first follow-up visit date is after the initial visit;
   (c) batch scheduling, by a processor-based device, the first follow-up batch visit for the plurality of patients by scheduling the first follow-up batch visit for each patient of the plurality of patients to occur in the first time window;
   (d) identifying a second follow-up visit date for a second follow-up batch visit for each patient of the plurality of patients, the second follow-up visit date for each of patient of the plurality of patients being within a second time window, wherein the second follow-up visit date is after the first follow-up visit date;
   (e) batch scheduling, by the processor-based device, the second follow-up batch visit for the plurality of patients by scheduling the second follow-up batch visit for each patient of the plurality of patients to occur in the second time window; and
   wherein the first time window and second time window are separated by at least one week.

2. The method of claim 1, wherein the initial visit, first follow-up batch visit, and second follow-up batch visit for the plurality of patients are associated with the clinical trial.

3. The method of claim 1, further comprising communicating the batch scheduled first follow-up visit date and batch scheduled second follow-up visit date to each patient of the plurality of patients.

4. The method of claim 3, wherein the communication is electronic.

5. The method of claim 1, wherein the method is used by a research site conducting research, and wherein the research site is able to prepare one or more of study supplies, patient charts, study goals, and data collecting requirements in preparation for at least one of the first follow-up batch visit or the second follow-up batch visit for the plurality of patients.

6. The method of claim 1, wherein the first time window and second time window each comprise one of: one day, one week, or one month.

7. The method of claim 1, further comprising:
   electronically generating a reminder for the first follow-up batch visit for the plurality of patients; and
   providing the reminder to each patient of the plurality of patients over a network.

8. The method of claim 1, wherein the nature of the first follow-up batch visit and the second follow-up batch visit for the plurality of patients relates to a protocol of the clinical trial.

9. The method of claim 1, further comprising:
   scheduling a first emergency visit between the initial visit and the first time window, wherein the first emergency visit comprises a first unscheduled visit by at least one of the plurality of patients.

10. The method of claim 1, wherein the initial visit occurs at a different time for each patient of the plurality of patients.

11. A system for scheduling a plurality of patients participating in a clinical trial by a batch scheduling process after an initial visit by each of the plurality of patients, the system comprising:
    a research site device comprising a processor capable of executing program code stored on computer-readable media, the research site device being configured to execute the program code to:
       determine a number of follow-up visits after an initial visit by each patient of the plurality of patients participating in the clinical trial conducted at a research site;
       batch schedule a first follow-up batch visit for each patient of the plurality of patients, the first follow-up batch visit for each patient of the plurality of patients being batch scheduled for a first follow-up visit date to occur in a first time window; and
       batch schedule a second follow-up batch visit for each patient of the plurality of patients, the second follow-up batch visit for each patient of the plurality of patients being batch scheduled for a second follow-up visit date to occur in a second time window,
    wherein the first time window and the second time window are configured to be separated by at least one week.

12. The system of claim 11, wherein the first follow-up batch visit and the second follow-up batch visit for the plurality of patients are associated with the clinical trial.

13. The system of claim 11, wherein the research site device is configured to provide the first follow-up visit date and the second follow-up visit date to the plurality of patients over a network.

14. The system of claim 11, wherein the first time window and the second time window each comprises one of: one day, one week, or one month.

15. The system of claim 11, wherein the first time window and the second time window are a condensed time span.

16. The system of claim 11, wherein the research site device is configured to generate a reminder for at least one of the first follow-up visit date or the second follow-up visit date for the plurality of patients and provide the reminder to each of the plurality of patients over a network.

17. A method for scheduling a plurality of patients participating in a clinical trial in batches, the method comprising:
    identifying a first time window in which to schedule a first follow-up batch visit for all of the plurality of patients to occur in a first batch, the first batch to be conducted during the first time window;
    identifying a second time window in which to schedule a second follow-up batch visit for all of the plurality of patients to occur in a second batch, the second batch to be conducted during the second time window;
    scheduling the first follow-up batch visit for each patient of the plurality of patients to occur in the first time window; and scheduling the second follow-up batch visit for each patient of the plurality of patients to occur in the second time window.

18. The method of claim 17, wherein the first time window and the second time window are at least one of: one hour, one day, or one week.

19. The method of claim 1, wherein the first time window and second time window each comprise one month; and wherein the first time window and the second time window are separated by at least ninety days.

20. The system of claim 11, wherein the first time window and the second time window comprise one month; and wherein the first time window and the second time window are configured to be separated by at least ninety days.

* * * * *